US010283979B1

(12) United States Patent
Grison

(10) Patent No.: US 10,283,979 B1
(45) Date of Patent: *May 7, 2019

(54) PHALLUS STORAGE RACK

(71) Applicant: Michell Roland Grison, Victoria (CA)

(72) Inventor: Michell Roland Grison, Victoria (CA)

( * ) Notice: Subject to any disclaimer, the term of this patent is extended or adjusted under 35 U.S.C. 154(b) by 0 days.

This patent is subject to a terminal disclaimer.

(21) Appl. No.: 15/904,776

(22) Filed: Feb. 26, 2018

(51) Int. Cl.
*A61L 2/10* (2006.01)
*H02J 7/02* (2016.01)
*A61H 19/00* (2006.01)
*A61H 37/00* (2006.01)
*H02J 7/00* (2006.01)

(52) U.S. Cl.
CPC ............ *H02J 7/0027* (2013.01); *A61H 37/00* (2013.01); *A61L 2/10* (2013.01); *H02J 7/0044* (2013.01); *H02J 7/02* (2013.01); *A61H 19/00* (2013.01)

(58) Field of Classification Search
CPC .......... H02J 7/0027; H02J 7/0044; H02J 7/02; A61H 37/00; A61H 19/00; A61L 2/10
USPC ............................ 250/453.11, 454.11, 455.11
See application file for complete search history.

(56) References Cited

PUBLICATIONS

Grison, "Phallus Storage Case", Nov. 25, 2017, co-pending U.S. Appl. No. 15/822,136 (Year:2017).*

* cited by examiner

*Primary Examiner* — Nicole M Ippolito
(74) *Attorney, Agent, or Firm* — Island IP Law; Stephen R. Burri

(57) ABSTRACT

A sex toy storage, charging, and sanitization device having a base with an internal electrical compartment; at least one phallus support rack extending upwardly from the base forming a plurality of phallus storage compartments; at least one electrical outlet embedded in the base adjacent each of the phallus storage compartments; at least one USB port embedded in the base adjacent each of the at least one phallus storage compartments; a string of ultraviolet 'C' frequency lights attached to the underside of the cover for sanitization; a supercharger for storing electrical power for recharging sex toys; an electric bar for recharging sex toys connected to the electrical outlet; a USB component for recharging sex toys connected to the USB port; an electrical cord for electrical connection to an external power source; three hooks for hanging sex toys from the rack; and a cover.

13 Claims, 5 Drawing Sheets

PHALLUS STORAGE RACK

FIELD OF THE INVENTION

The present invention relates to a sex toy accessory. In particular, the present invention relates to storage, charging and sanitizing of sex toys.

BACKGROUND OF THE INVENTION

It is known to provide a variety of sex toys, including phalluses, for entertainment purposes. Many such phalluses are electric and require batteries or are rechargeable.

It is desirable to provide a convenient, discrete apparatus for storage of phalluses. It is also desirable to provide means for discretely sanitizing and recharging the phalluses and batteries which may be used to operate the phalluses.

BRIEF DESCRIPTION OF THE DRAWINGS

A detailed description of the preferred embodiments is provided below by way of example only and with reference to the following drawings, in which.

Figure 1:
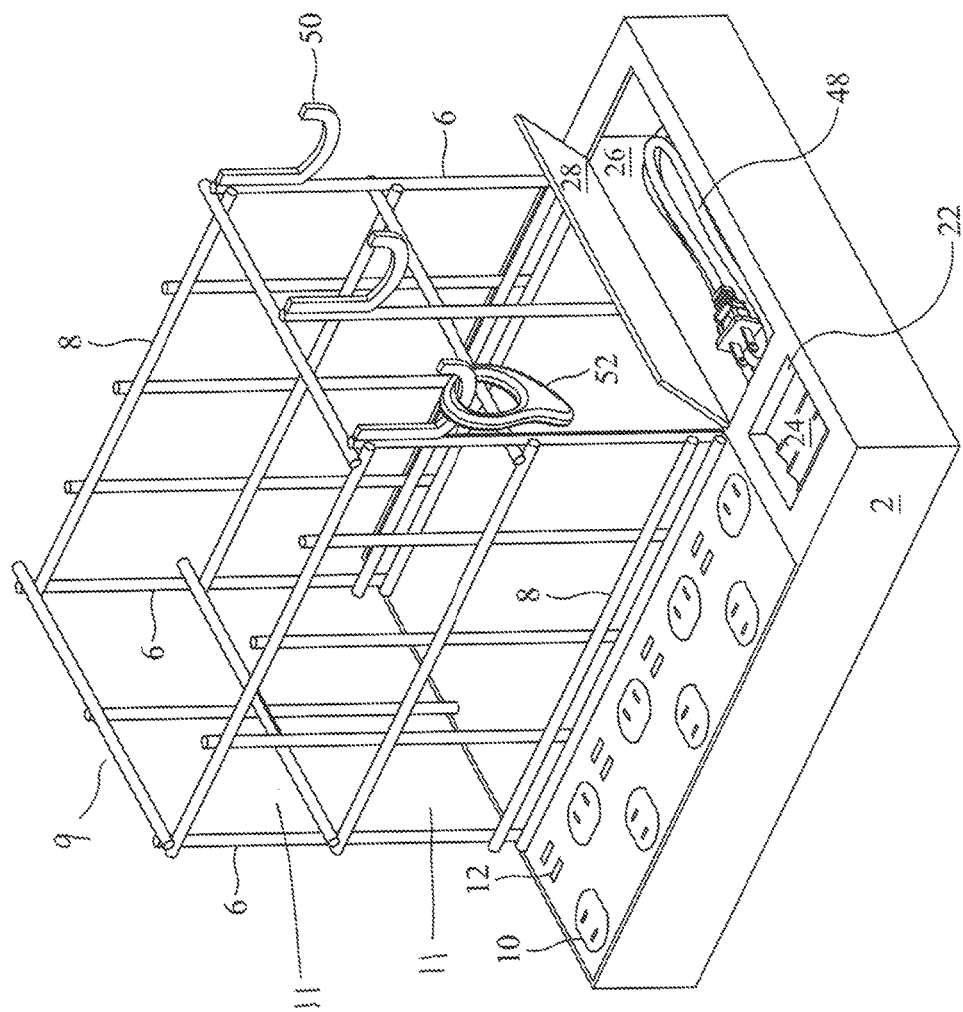
FIG. 1 is an upper perspective view of a preferred embodiment of the base of the present invention, with the electrical cord compartment open.

In the drawings, several embodiments of the invention are illustrated by way of example. It is to be expressly understood that the description and drawings are only for the purpose of illustration and as an aid to understanding and are not intended as a definition of the limits of the invention.

SUMMARY OF THE INVENTION

A sex toy storage and charging device comprising a base having an internal electrical compartment; at least one phallus support rack extending upwardly from the base, the rack forming at least one phallus storage compartment; at least one electrical outlet embedded in the base adjacent each of the at least one phallus storage compartments; a USB port embedded in the base adjacent each of the at least one phallus storage compartments; a supercharger for storing electrical power for recharging sex toys; an electric bar for recharging sex toys connected to the electrical outlet; a USB component for recharging sex toys connected to the USB port; an electrical cord for electrical connection to an external power source; and a cover.

The device may include means for sanitization of sex toys stored therein using a string of ultraviolet 'C' frequency lights attached to the underside of the cover.

The sex toy device may have at least four vertical posts and four perpendicular horizontal posts forming a rack having a plurality of phallus storage compartments, and preferably has eight phallus storage compartments.

There may be a rechargeable battery compartment and an electrical cord compartment embedded in the upper side of the base, and an electrical compartment embedded in the lower side of the based, the cord compartment and electrical compartments preferably having rotatable covers.

The cover may include at least one external handle and locking means for locking the cover to the base, preferably a number tumbler lock. The sex toy device of the present invention is manufactured primarily of antimicrobial plastic.

DESCRIPTION OF THE INVENTION

As depicted in the drawings, the present invention comprises an apparatus for storage, charging, and sanitization of sex toys, in particular, phalluses. The apparatus comprises a base 2 and a cover 4.

As may be best seen in FIG. 1, the base further comprises a plurality of vertical posts 6 and horizontal posts 8 forming a rack 9 having a plurality of storage compartments 11. In the preferred embodiment, 8 storage compartments are provided in four vertically stacked pairs of storage compartments. Adjacent each vertically stacked pair of storage compartments there is provided two electrical outlets 10 and two USB ports 12 for insertion of recharging plugs or USB cords, respectively.

Figure 2:
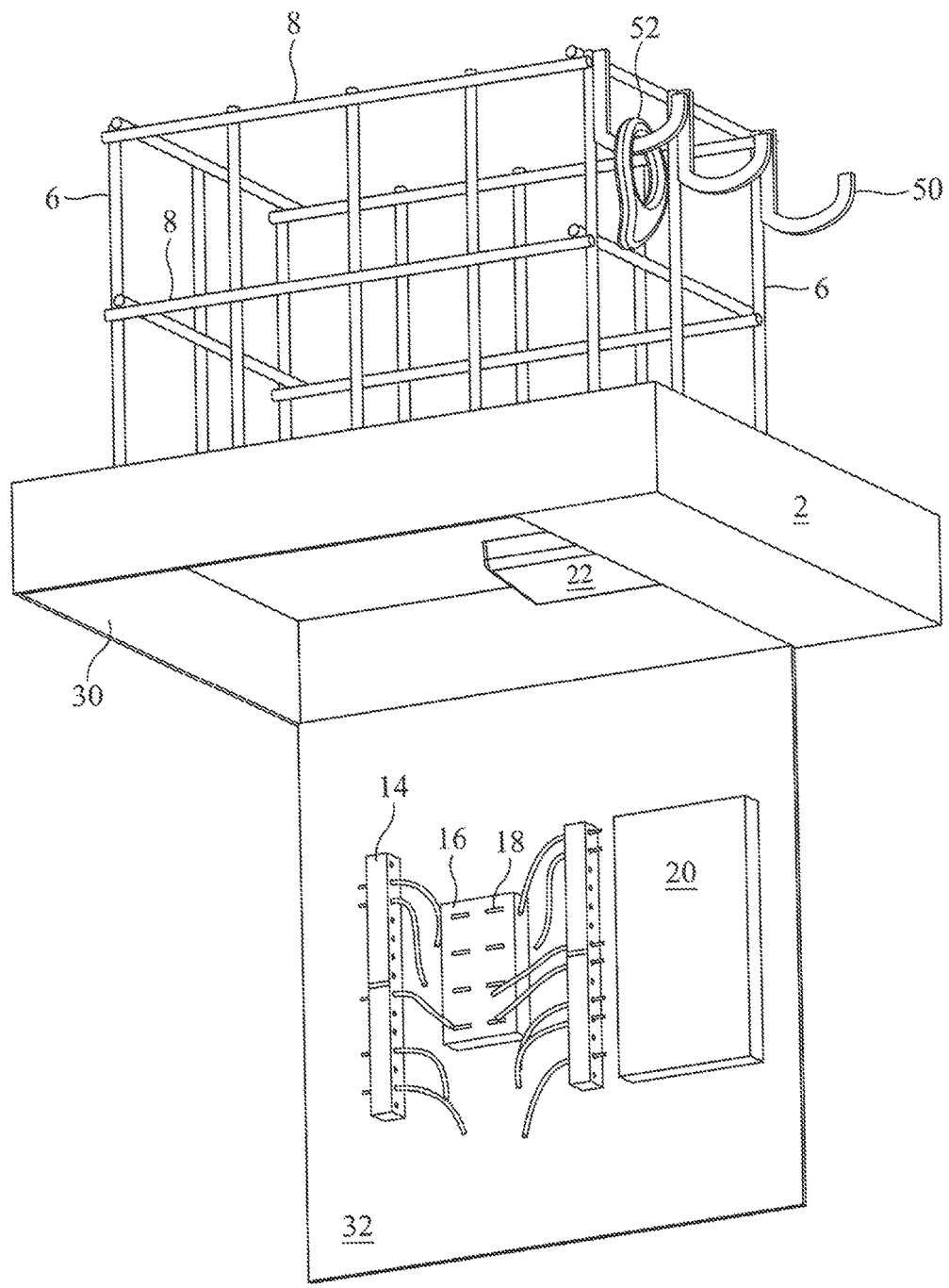
FIG. 2 is a lower perspective view of the preferred embodiment of the base of the present invention, with the electrical compartment open.

With reference to FIG. 2, the base further comprises one or more electric bars 14 and a USB component 16 having 8 USB ports 18. A supercharger battery 20 is also stored in the electrical compartment. The electrical compartment 30 has a rotatable cover 32 to provide access to the electrical components.

On the upper side of the base, there is further provided a battery compartment 22 with slots 24 for recharging 4 "AA" type batteries. An electrical cord compartment 26 with raiseable lid 28 is used for storage of an electrical cord 48 for connection of the apparatus to an AC electric power source. Extending from the upper edge of one side of the rack may be provided three hooks 50. FIG. 2 depicts a sex toy 52 removably suspended from one of the hooks.

Preferably, the base and cover of the invention are manufactured of antimicrobial plastic, but other materials are also possible.

Figure 3:
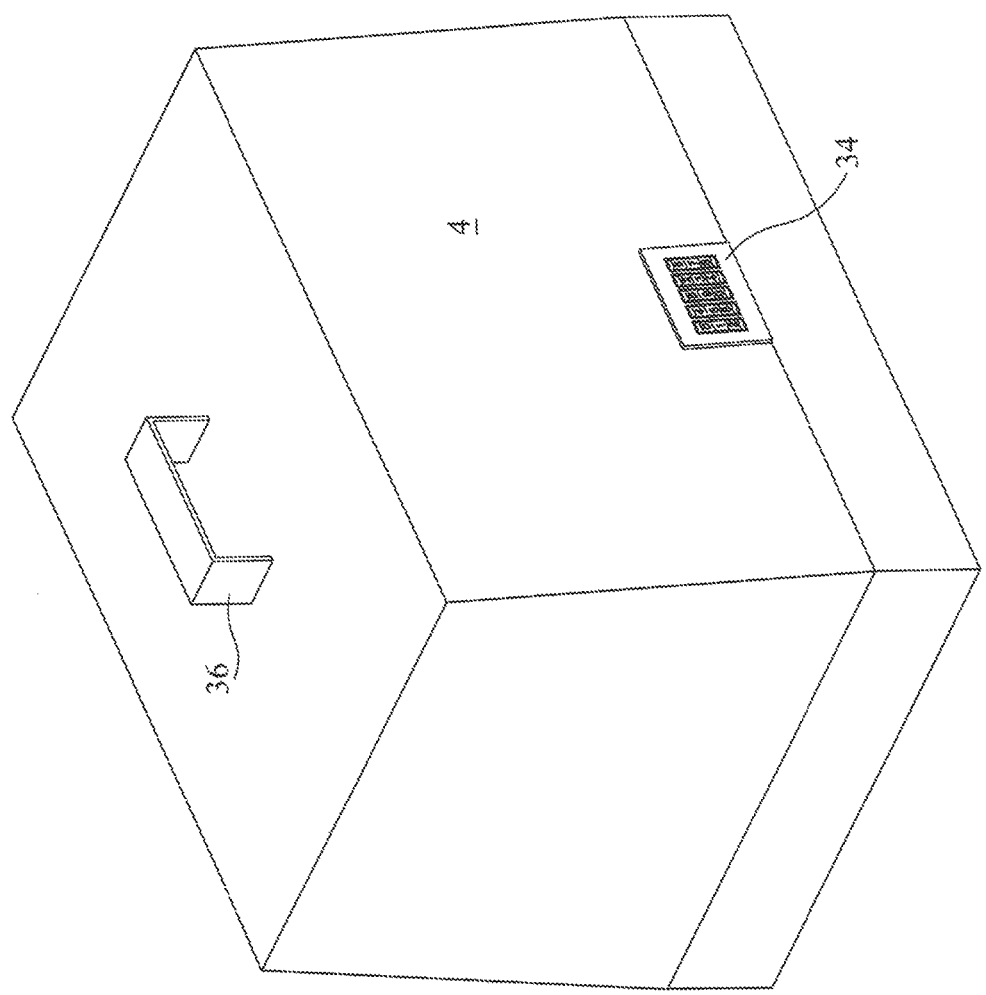
FIG. 3 is an upper perspective view of the cover of the present invention.
Figure 4:
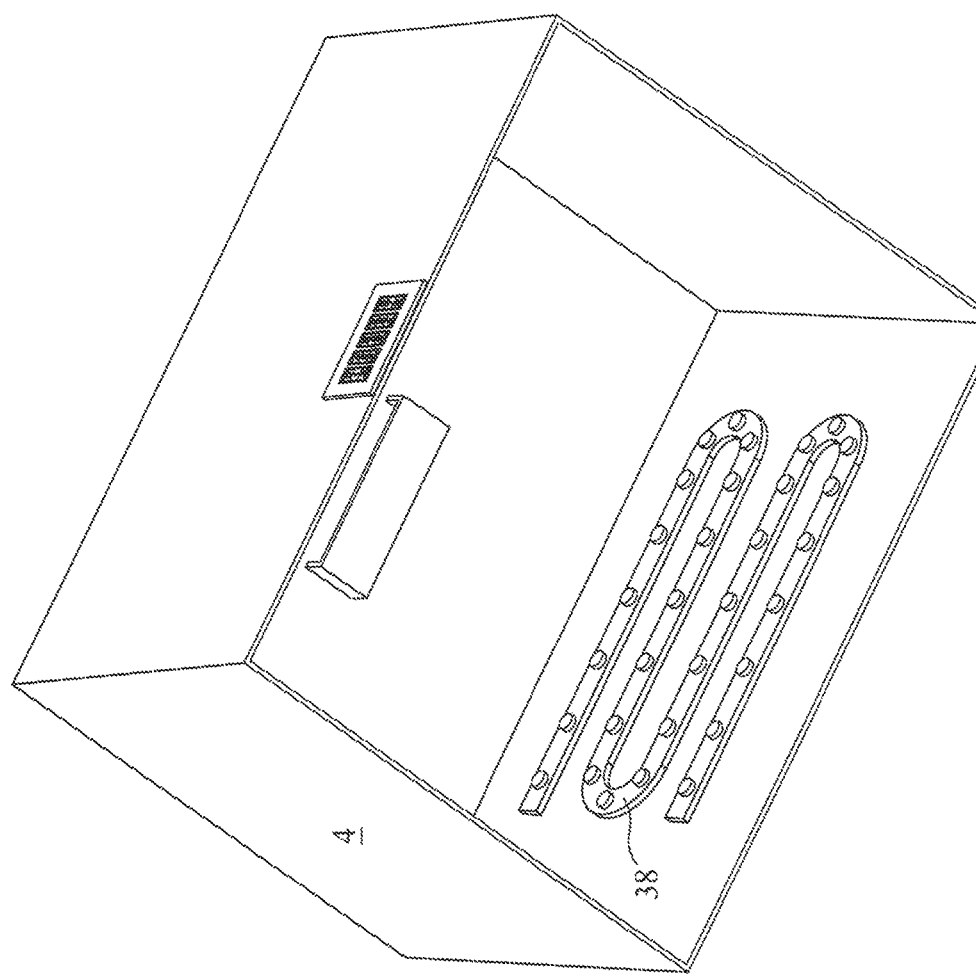
FIG. 4 is a lower perspective view of the cover of the present invention.

As shown in FIGS. 3 and 4, the cover 4 of the invention is provided with a number tumbler lock 34 and an upper handle 36. Other locking means are also possible within the scope of the invention. Various cover shapes are also possible within the scope of the invention.

Figure 5:
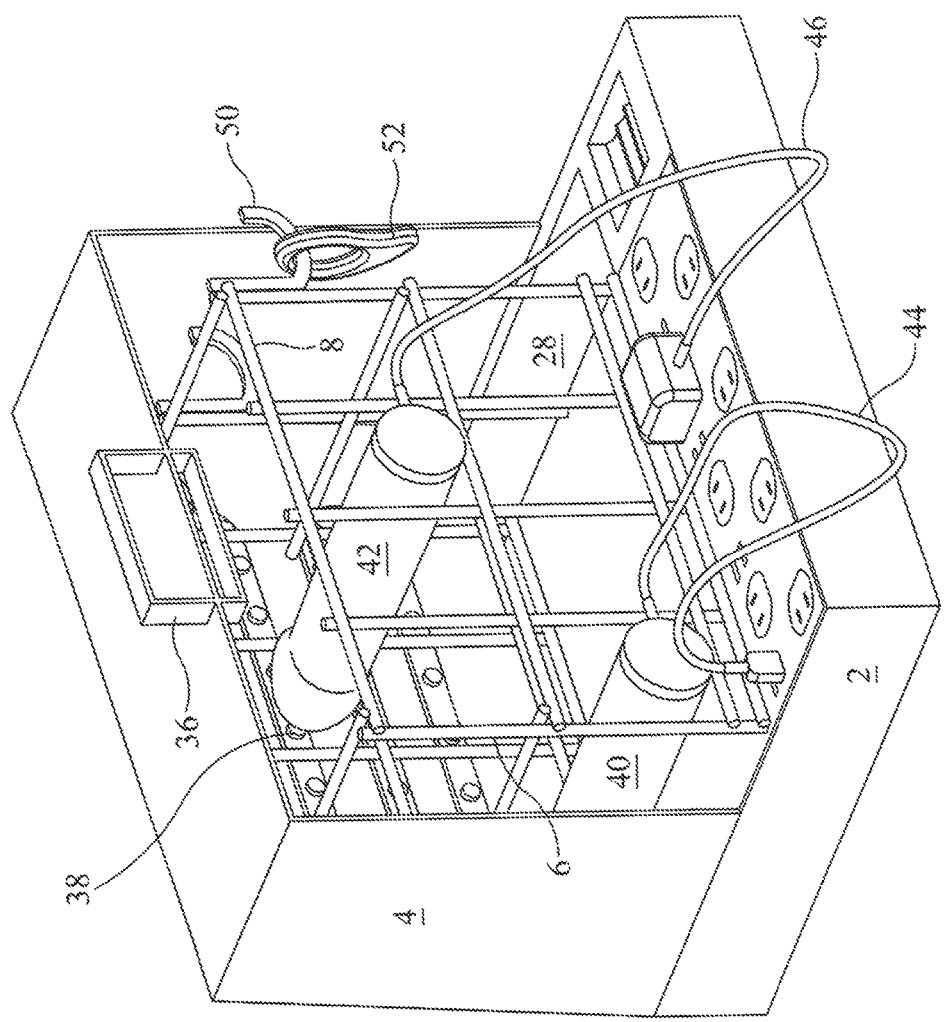
FIG. 5 is a cutaway view of a the base and cover of the invention, showing two sex toys stored in the rack.

As may be seen in FIGS. 4 and 5, a string of germicidal ultraviolet 'C' frequency ("UVC") lights 38 is disposed along the inside back of the cover to provide sanitizing UV radiation to the phalluses stored in the device. UVC light will destroy 99.9% of bacteria and viruses on the phalluses.

In operation, one or more phalluses 40, 42 each are placed in a selected storage compartment of the rack. Each USB charging cord 44 is inserted into the corresponding USB port, and each electrical charging cord 46 is inserted into the corresponding electric outlet. The cover is placed over the base and the apparatus is connected to an external power source. Each of the phalluses will be recharged while being stored in the device. In addition, the siring of lights will sanitize each phallus, rendering it clean and ready for use.

Other uses for the device are also possible. For example, any small electrical device may be recharged in the device, including mobile phones, cameras, electric toothbrushes, shavers, laptops, and other devices. Also, any object, may be sanitized in the device using the UVC light.

As many possible embodiments may be made of the invention without departing from the scope of the claims, it is to be understood that all matter herein set forth or shown in the accompanying drawings is to be interpreted as illustrative and not in a limiting sense.

It will be appreciated by those skilled in the art that other variations of the preferred embodiment may also be practised without departing from the scope of the invention.

The invention claimed is:

1. A sex toy storage and charging device comprising:
   a. a base having an internal electrical compartment;
   b. at least one phallus support rack extending upwardly from the base, the rack forming at least one phallus storage compartment;
   c. at least one electrical outlet embedded in the base adjacent each of the at least one phallus storage compartments;
   d. a USB port embedded in the base adjacent each of the at least one phallus storage compartments;
   e. a supercharger for storing electrical power for recharging sex toys;
   f. an electric bar for recharging sex toys connected to the electrical outlet;
   g. a USB component for recharging sex toys connected to the USB port;
   h. an electrical cord for electrical connection to an external power source; and
   i. a cover.

2. The sex toy device of claim 1, further comprising at least one hook extending from one side of the phallus support rack for removably attaching sex toys to the rack.

3. The sex toy device of claim 1, further comprising means for sanitization of sex toys stored therein.

4. The sex toy device of claim 1, wherein the at least one phallus storage compartment comprises eight phallus storage compartments.

5. The sex toy device of claim 1, further comprising a rechargeable battery compartment embedded in the upper side of the base.

6. The sex toy device of claim 1, wherein the phallus support rack comprises at least four vertical posts and at least four perpendicular horizontal posts.

7. The sex toy device of claim 1, further comprising an electrical cord compartment embedded in the upper side of the base, the electrical cord compartment having a cover.

8. The sex toy device of claim 1, further comprising an electrical compartment embedded in the lower side of the base, the electrical compartment having a cover.

9. The sex toy device of claim 1, wherein the means for sanitization of sex toys comprises a string of ultraviolet 'C' frequency lights attached to the underside of the cover.

10. The sex toy device of claim 1, wherein the cover further comprises at least one external handle.

11. The sex toy device of claim 1, wherein the cover further comprises means for locking the cover to the base.

12. The sex toy device of claim 11, wherein the locking means comprises a number tumbler lock.

13. The sex toy device of claim 1, wherein the device is manufactured of antimicrobial plastic.

* * * * *